United States Patent [19]

Giselbrecht et al.

[11] Patent Number: 5,872,153
[45] Date of Patent: Feb. 16, 1999

[54] PROCESS FOR PREPARING AQUEOUS O-PHTHALALDEHYDE-GLUTARALDEHYDE SOLUTIONS

[75] Inventors: Karl Heinz Giselbrecht, Pasching; Eduard Perndorfer, Traun, both of Austria

[73] Assignee: DSM Chemie Linz GmbH, Austria

[21] Appl. No.: 979,952

[22] Filed: Nov. 26, 1997

[30] Foreign Application Priority Data

Nov. 26, 1996 [AT] Austria .................................. A 2053/96

[51] Int. Cl.⁶ ............................ A01N 35/00; C07C 45/00
[52] U.S. Cl. ............................. 514/699; 568/426; 568/438
[58] Field of Search ........................... 514/699; 568/438, 568/426

[56] References Cited

U.S. PATENT DOCUMENTS 5,128,051  7/1992  Theis et al. .

5,326,438  7/1994  Hermeling .

OTHER PUBLICATIONS

*Chemical Abstracts*, vol. 121, Abstract No. 121:280381s(1994).

*Primary Examiner*—Alan Siegel
*Attorney, Agent, or Firm*—Wenderoth, Lind & Ponack

[57] ABSTRACT

A process for preparing an aqueous o-phthalaldehyde-glutaraldehyde solution which comprises converting an acetal of the o-phthalaldehyde in a 10 to 60% strength aqueous glutaraldehyde solution into o-phthalaldehyde at room temperature up to 100° C. by eliminating the corresponding alcohol, and removing the eliminated alcohol to give the aqueous o-phthalaldehyde-glutaraldehyde solution.

9 Claims, No Drawings

PROCESS FOR PREPARING AQUEOUS O-PHTHALALDEHYDE-GLUTARALDEHYDE SOLUTIONS

Aqueous o-phthalaldehyde-(OPA)-glutaraldehyde solutions have hitherto been prepared by simply dissolving crystalline OPA in an aqueous glutaraldehyde solution, and are used, for example, for preparing biocides (U.S. Pat. No. 5,128,051).

OPA exists in crystalline form and, in this form, has several disadvantages since it is poisonous and leads to skin irritation, making handling of OPA difficult. Furthermore, OPA tends, over prolonged storage periods, to block, as a result of which lengthy detachment processes are required which may possibly lead to discoloration of the OPA.

The object of the present invention was therefore to find a preparation method for aqueous OPA-glutaraldehyde solutions which avoids direct handling of crystalline OPA and the disadvantages associated with OPA storage.

Surprisingly, this object can be achieved by a process in which the aqueous OPA-glutaraldehyde solution is obtained by cleavage of an OPA acetal in aqueous glutaraldehyde solution.

The present invention accordingly provides a process for preparing an aqueous o-phthalaldehyde-glutaraldehyde solution which comprises converting an acetal of the o-phthalaldehyde in a 10 to 60% strength aqueous glutaraldehyde solution into o-phthalaldehyde at room temperature up to 100° C. by eliminating the corresponding alcohol, and removing the eliminated alcohol to give the aqueous o-phthalaldehyde-glutaraldehyde solution.

The process according to the invention uses an OPA acetal as starting material. Examples of suitable acetals are dialkoxyphthalans or tetraalkyl acetals of OPA having, preferably, from 1 to 4 carbon atoms in the alkoxy moiety. Particular preference is given to using dialkoxyphthalans.

Tetraalkyl acetals of OPA are described, for example, in U.S. Pat. No. 5,326,438. The corresponding dialkoxyphthalan can be obtained, for example, by a process which uses, for example, unpurified OPA as starting material. For this, a solution of an OPA, obtained by any desired preparation process, in an alcohol having from 1 to 4 carbon atoms is firstly prepared. Alcohols having, preferably, from 1 to 4 carbon atoms are methanol, ethanol, propanol and butanol. Preference is given to methanol and ethanol, and particular preference to methanol.

OPA can, for example, be prepared from dimethoxybenzene by an electrochemical route or by ozonolysis of naphthalene. Preference is given to an OPA prepared by ozonolysis, for example according to U.S. Pat. No. 4,769,464. If an OPA prepared by ozonolysis of naphthalene is used as starting material, it is already in the form of an alcoholic solution after ozonolysis, reduction of the peroxides and subsequent removal of the catalyst.

In addition to the unpurified OPA, this solution also contains naphthalene, phthalide, methoxyphthalan, and aldehydic acids and aldehydic esters, such as glyoxal, glycolates or glyoxylates, or fragments thereof or their sodium salts, the degree of impurity being between 5 and 90%, depending on the quality of the hydrogenation catalyst. The process is independent of the nature and the content of impurities.

The alcoholic solution containing the unpurified OPA is then adjusted to a pH between 0 and 3, preferably between 0.5 and 2, by acidification. Suitable acidifiers are mineral acids, such as HCl, $H_2SO_4$, $H_3PO_4$, organic acids, such as formic acid, acetic acid, p-toluenesulfonic acid or methyl-sulfonic acid, or acidic ion exchangers. Preference is given to mineral acids, and particular preference to $H_2SO_4$. The temperature in this step is from 0° to 65° C., preferably from 15° to 30° C. Acidification converts the OPA to be purified into the corresponding dialkoxyphthalan.

Any sodium sulfate precipitate that forms may be removed and the remaining solution of the phthalan formed is mixed with up to 50% strength aqueous alkali solution in the next step. Examples of suitable alkali solutions are sodium hydroxide solution or potassium hydroxide solution. Preference is given to sodium hydroxide solution.

The alcohol used as solvent is subsequently or simultaneously distilled off. The chosen pressure and temperature depend on the alcohol used. Distilling off the alcohol leaves a salt solution containing the phthalan. If solid salts are present in this solution, it is diluted with water in order to dissolve these salts.

While the impurities such as esters, acids etc., remain in the aqueous phase as sodium salts, the corresponding dialkoxyphthalan is extracted from the organic phase using common extractants, such as, for example, ethers, for example diethyl ether, diisopropyl ether, methyl tert-butyl ether etc., or using ethyl acetate or toluene etc.

Preferred extractants are methyl tert-butyl ether, ethyl acetate and toluene. The chosen temperature during the extraction process is dependent on the extractant used and is preferably between room temperature and 80° C.

The resultant dialkoxyphthalan can be purified by distillation, after which it is in the form of a colorless liquid which can be stored indefinitely at room temperature.

The amount of acetal used depends on the desired end concentration of OPA in the glutaraldehyde solution. Using the process according to the invention it is possible to obtain glutaraldehyde solutions having an OPA content of up to 30% by weight. The aqueous glutaraldehyde solution used is a 10 to 60% strength by weight solution, preferably a 30 to 55% strength by weight solution.

An amount of acetal which corresponds to the desired end concentration of OPA is then mixed with the aqueous glutaraldehyde solution. The mixture is then further diluted with sufficient water for the concentration of the glutaraldehyde solution to remain constant during the subsequent distillation of the eliminated alcohol. The reaction temperature depends on the alkoxy radical in the acetal and is preferably between room temperature and 100° C. The reaction to give OPA can also be carried out at a pressure from normal pressure to a pressure of 300 mbar, preferably up to a pressure of 200 mbar, depending on the alkoxy radical.

The alcohol which is eliminated is then distilled off under reduced pressure. Water may again be added to maintain a constant concentration. The resulting aqueous OPA-glutaraldehyde solution can be adjusted to an OPA content of from 1 to 30% by weight, preferably from 1 to 10% by weight, by further dilution with glutaraldehyde solution, and can be used directly, for example, for biocide preparation.

EXAMPLE 1

900 ml of glutaraldehyde (50% strength aqueous solution, Union Carbide, UN 1760), 100 ml of unpurified yellowish dimethoxyphthalan (obtained from the OMPA plant of DSM Chemie Linz) and 500 ml of demineralized water were mixed (pH 3.58), and 1228 g of a water/methanol mixture were drawn off via the head under a vacuum of 200 mbar over the course of 6.5 hours. A further 900 g of demineralized water were added dropwise simultaneously. The still temperature was 60.9° C., and the head temperature was 59.4° C. A further 250 g of demineralized water were then added dropwise and again distilled off via the head. The still temperature was 61.1° C., and 1315 g of solution having a pH of 3.47 remained in the still. The head temperature was 59.7° C. and 189 g of distillate were obtained. The end point of the reaction was determined using GC and complete cleavage was reached at a content of <0.1 area % of acetal. 100 g of the still solution were mixed with 107. g of 50% strength aqueous glutaraldehyde solution to give an OPA content of approximately 3% by weight. The color number of this aqueous OPA-glutaraldehyde solution was determined: H=76

EXAMPLE 2

900 ml of glutaraldehyde (50% strength aqueous solution, Union Carbide) and 100 ml of distilled colorless dimethoxyphthalan (from the OMPA plant of DSM Chemie Linz) were mixed and 500 g of demineralized water were added thereto. A water/methanol mixture was then drawn off at 200 mbar via the head, a further 1000 g of demineralized water being slowly added dropwise during the first 4 hours. The still temperature was 60.3°–61.3° C. and the head temperature was 59.6°–59.9° C. After 7 hours, 1103 g of solution were obtained in the still and 1468 g of distillate were obtained. The still solution contained approximately 7.4% by weight of OPA and approximately 48% of water.

100 g of still solution were diluted with 148 g of 50% strength glutaraldehyde solution to give an OPA content of approximately 3% by weight.

The color number of the dilute solution was determined:

H=58

As comparison, a solution of 3% by weight of OPA in 50% strength glutaraldehyde solution was prepared by simply dissolving the corresponding amount of OPA, and the color number was determined: H=71

EXAMPLE 3

800 ml of glutaraldehyde (50% strength aqueous solution, Union Carbide) were mixed with 200 ml of freshly distilled dimethoxyphthalan (from the OMPA plant of DSM Chemie Linz), 500 ml of demineralized water were added thereto and a water/methanol mixture was drawn off at 200 mbar via the head. During the first 4 hours of distillation, a further 1000 ml of demineralized water were slowly added dropwise. The still temperature was 61.2°–61.4° C. and the head temperature was 59.1°–61.1° C. After 7 hours 1434 g of distillate were obtained. A further 500 g of water were then added dropwise and distillation was continued for a further 9 hours. 513 g of distillate were drawn off and 1137 g of still solution were obtained. The still solution contained approximately 14.6% by weight of OPA and approximately 45% of water. 100 g of still solution were diluted with 386.6 g of 50% strength glutaraldehyde solution to give an OPA content of approximately 3% by weight. The color number of the dilute solution was determined: H=58

EXAMPLE 4

700 ml of glutaraldehyde (50% aqueous solution, Union Carbide) were mixed with 300 ml of freshly distilled dimethoxyphthalan (from the OMPA plant of DSM Chemie Linz), and 500 ml of demineralized water were added thereto. A water/methanol mixture was then drawn off at 200 mbar via the head, a further 1500 g of water being slowly added dropwise over the course of the first 6 hours.

Still temperature: 60.1° C.–61.4° C.

Head temperature: 59.2° C.–60.9° C.

After 9 hours 1765 g of distillate were obtained. A further 1250 g of water were added dropwise over the course of 5 hours and distillation was carried out simultaneously. After 16 hours a further 1481 g of distillate were obtained. A total of 1096 g of still solution were obtained which contained approximately 22.3% by weight of OPA and approximately 40.5% of water. 100 g of still solution were diluted with 656.6 g of 50% strength glutaraldehyde solution to give an OPA content of approximately 3% by weight. The color number of this solution was determined: H=62.

We claim:

1. A process for preparing an aqueous o-phthalaldehyde-glutaraldehyde solution, which comprises converting an acetal of the o-phthalaldehyde in a 10 to 60% strength aqueous glutaraldehyde solution into o-phthalaldehyde at room temperature up to 100° C. by eliminating the corresponding alcohol, and removing the eliminated alcohol to give the aqueous o-phthalaldehyde-glutaraldehyde solution.

2. The process as claimed in claim 1, wherein the acetal used is a tetraalkyl acetal or a dialkoxyphthalan, each having from 1 to 4 carbon atoms in the alkoxy moiety.

3. The process as claimed in claim 2, wherein a dialkoxyphthalan is used as acetal.

4. The process as claimed in claim 1, wherein a 30 to 55% strength by weight aqueous glutaraldehyde solution is used.

5. The process as claimed in claim 1, wherein the reaction is carried out at a pressure from normal pressure to 300 mbar.

6. The process as claimed in claim 5, wherein the reaction is carried out at a pressure from normal pressure to 200 mbar.

7. The process as claimed in claim 1, wherein sufficient water is added to the reaction solution during distillation of the eliminated alcohol to keep the concentration of the glutaraldehyde solution constant.

8. The process as claimed in claim 1, wherein the acetal is used in an amount which leads to an o-phthalaldehyde content of from 1 to 30% by weight in the aqueous glutaraldehyde solution.

9. The process as claimed in claim 8, wherein the acetal is used in an amount which leads to an o-phthalaldehyde content of from 1 to 10% by weight in the aqueous glutaraldehyde solution.

* * * * *